United States Patent
Yanagisawa et al.

(10) Patent No.: US 7,166,735 B2
(45) Date of Patent: Jan. 23, 2007

(54) ORGANOSILICON COMPOUND, MAKING METHOD, AND RUBBER COMPOUNDING AGENT

(75) Inventors: Hideyoshi Yanagisawa, Gunma-ken (JP); Masaaki Yamaya, Gunma-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 279 days.

(21) Appl. No.: 10/464,492

(22) Filed: Jun. 19, 2003

(65) Prior Publication Data
US 2003/0236424 A1 Dec. 25, 2003

(30) Foreign Application Priority Data
Jun. 20, 2002 (JP) .............................. 2002-180441

(51) Int. Cl.
*C07F 7/08* (2006.01)
(52) U.S. Cl. .................. 556/427; 524/155; 524/262
(58) Field of Classification Search ................ 556/427; 524/155, 262
See application file for complete search history.

(56) References Cited

U.S. PATENT DOCUMENTS

| | | |
|---|---|---|
| 3,997,356 A | 12/1976 | Thurn et al. |
| 4,072,701 A | 2/1978 | Pletka et al. |
| 4,076,550 A | 2/1978 | Thurn et al. |
| 5,663,226 A * | 9/1997 | Scholl et al. ............... 524/262 |
| 5,827,912 A * | 10/1998 | Scholl ....................... 524/155 |
| 6,046,349 A | 4/2000 | Batz-Sohn et al. |
| 6,331,605 B1 | 12/2001 | Lunginsland et al. |
| 6,380,411 B1 | 4/2002 | Luginsland et al. |

FOREIGN PATENT DOCUMENTS

| | | |
|---|---|---|
| EP | 0 670 347 A1 | 9/1995 |
| EP | 0 748 839 A1 | 12/1996 |
| JP | 2001-226383 A | 8/2001 |
| JP | 2002-88088 A | 3/2002 |
| JP | 2002-145890 A | 5/2002 |

* cited by examiner

*Primary Examiner*—Samuel Barts
(74) *Attorney, Agent, or Firm*—Birch, Stewart, Kolasch & Birch, LLP

(57) ABSTRACT

Organosilicon compounds having organooxysilyl groups at ends and a polysulfide group at an intermediate of the molecule, which are linked through a divalent hydrocarbon group containing a monosulfide or polysulfide group are novel. These organosilicon compounds are effective as a rubber compounding agent.

10 Claims, No Drawings

ORGANOSILICON COMPOUND, MAKING METHOD, AND RUBBER COMPOUNDING AGENT

This nonprovisional application claims priority under 35 U.S.C. § 119(a) on Patent Application No(s). 2002-180441 filed in JAPAN on Jun. 20, 2002, which is(are) herein incorporated by reference.

This invention relates to a novel organosilicon compound having an organooxysilyl group at each end of the molecule and a polysulfide group at an intermediate of the molecule, which are linked through a divalent hydrocarbon group containing a monosulfide or polysulfide group; a method for preparing the same, and a compounding agent for rubber.

BACKGROUND OF THE INVENTION

Compounds containing alkoxysilyl groups and a polysulfide group within the molecule are known from the past. These compounds are utilized as an interfacial binder between inorganic materials (such as silica, aluminum hydroxide, talc and clay) and organic materials (such as thermoplastic resins, thermosetting resins and rubber), as an adhesion improver for rubber to inorganic substrates, and in primer compositions.

Rubber compositions in which various rubbers are loaded with silica are also known in the art. These rubber compositions are used for tire treads featuring low heat generation and improved abrasion resistance. It is well known in the art that compounds containing alkoxysilyl groups and a polysulfide group within the molecule, for example, bis (triethoxysilylpropyl) tetrasulfide and bis(triethoxysilylpropyl) disulfide are effective to these rubber compositions. The addition of such compounds, however, is still insufficient to the desire of further improving tensile strength, resilience and low heat generation.

SUMMARY OF THE INVENTION

An object of the present invention is to provide a novel organosilicon compound effective for improving properties (such as low heat generation and resilience) of silica-loaded vulcanizable rubber compositions; a method for preparing the same; and a rubber compounding agent comprising the same.

Aiming to develop a novel rubber compounding agent that when compounded in a silica-loaded vulcanizable rubber composition, can improve the vulcanized physical properties thereof, we have discovered that an organosilicon compound of the average compositional formula (1), shown below, is prepared by the method described below and is effective as a compounding agent for organic/inorganic composite materials and a filler treating agent and especially as a rubber compounding agent.

In a first aspect, the present invention provides an organosilicon compound of the average compositional formula (1):

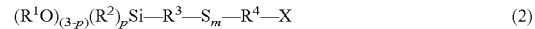  (1)

wherein $R^1$ and $R^2$ each are a monovalent hydrocarbon group having 1 to 4 carbon atoms, $R^3$ and $R^4$ each are a divalent hydrocarbon group having 1 to 15 carbon atoms, m is a positive number of 1 to 3 on average, n is a positive number of 2 to 4 on average, p is 0, 1 or 2, and q is 1, 2 or 3.

In a second aspect, the present invention provides a method for preparing an organosilicon compound of the average compositional formula (1). It is prepared by reacting a halogen-terminated organosilicon compound of the general formula (2):

  (2)

wherein $R^1$, $R^2$, $R^3$, $R^4$, m and p are as defined above, X is a halogen atom, with an anhydrous alkali metal sulfide or anhydrous alkali metal polysulfide of the general formula (3):

$$M_2S_r \quad (3)$$

wherein M is an alkali metal and r is a positive number of 1 to 4 on average, and optionally a halogen-containing compound of the general formula (4):

$$X-R^4-X \quad (4)$$

wherein $R^4$ and X are as defined above and/or sulfur.

A third aspect of the invention is a rubber compounding agent comprising an organosilicon compound of the average compositional formula (1). The compounding agent may comprise the organosilicon compound alone, or in admixture with a powder, or in admixture with another compounding agent.

In the embodiment wherein the compounding agent contains in admixture the organosilicon compound and at least one powder, the organosilicon compound and the powder are preferably in a weight ratio between 70/30 and 5/95.

DESCRIPTION OF THE PREFERRED EMBODIMENTS

The organosilicon compounds of the present invention have the average compositional formula (1).

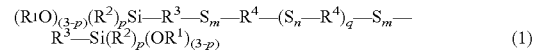  (1)

Herein $R^1$ and $R^2$ are independently selected from monovalent hydrocarbon groups having 1 to 4 carbon atoms, for example, alkyl groups such as methyl, ethyl, n-propyl, i-propyl, n-butyl, i-butyl and t-butyl, and alkenyl groups such as allyl and methallyl. $R^3$ and $R^4$ are independently selected from divalent hydrocarbon groups having 1 to 15 carbon atoms, for example, alkylene groups, arylene groups, and combinations thereof, such as methylene, ethylene, propylene, n-butylene, i-butylene, hexylene, decylene, phenylene and methylphenylethylene. The subscript m is a positive number of 1 to 3 on average, n is a positive number of 2 to 4 on average, p is 0, 1 or 2, and q is 1, 2 or 3.

Typical examples of the compounds of the average compositional formula (1) are given below.

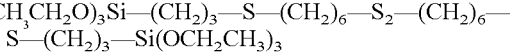
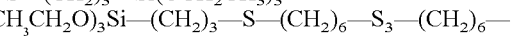
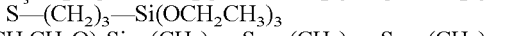
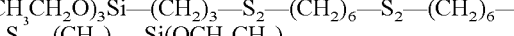
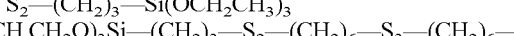
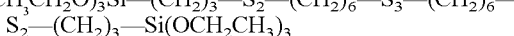
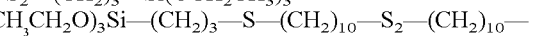
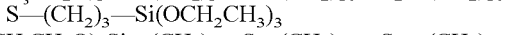
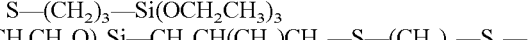
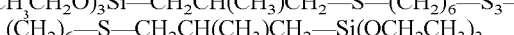
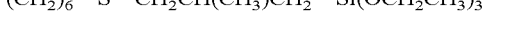

(CH₃CH₂O)₃Si—(CH₂)₃—S—(CH₂)₄—S₄—(CH₂)₄—S—(CH₂)₃—Si(OCH₂CH₃)₃

(CH₃CH₂O)₃Si—(CH₂)₃—S₃—(CH₂)₄—S₃—(CH₂)₄—S₃—(CH₂)₃—Si(OCH₂CH₃)₃

(CH₃CH₂O)₃Si—(CH₂)₆—S—(CH₂)₆—S₂—(CH₂)₆—S—(CH₂)₆—Si(OCH₂CH₃)₃

(CH₃CH₂O)₃Si—(CH₂)₃—S—(CH₂)₆—(S₂—(CH₂)₆)₂—S—(CH₂)₃—Si(OCH₂CH₃)₃

(CH₃CH₂O)₃Si—(CH₂)₃—S—(CH₂)₆—(S₂—(CH₂)₆)₃—S—(CH₂)₃—Si(OCH₂CH₃)₃

(CH₃CH₂O)₃Si—(CH₂)₃—S—(CH₂)₄—(S₂—(CH₂)₄)₂—S—(CH₂)₃—Si(OCH₂CH₃)₃

(CH₃O)₃Si—(CH₂)₃—S—(CH₂)₆—S₂—(CH₂)₆—S—(CH₂)₃—Si(OCH₃)₃

(CH₃CH₂O)₂CH₃Si—(CH₂)₃—S—(CH₂)₆—S₂—(CH₂)₆—S—(CH₂)₃—SiCH₃(OCH₂CH₃)₂

In the above-described compounds, S generally has a distribution because of disproportionation reaction or the like, so that its number is described essentially as an average value. In the average compositional formula (1), m has an average value of 1 to 3, preferably 1 or 2, and more preferably 1; n has an average value of 2 to 4, preferably 2 to 3. It is also preferred that m and n are m≦n, and more preferably m<n.

The organosilicon compound of the average compositional formula (1) can be prepared by reacting a halogen-terminated organosilicon compound of the general formula (2):

$$(R^1O)_{(3-p)}(R^2)_pSi—R^3—S_m—R^4—X \qquad (2)$$

with an anhydrous alkali metal sulfide or anhydrous alkali metal polysulfide of the general formula (3):

$$M_2S_r \qquad (3),$$

and optionally a halogen-containing compound of the general formula (4):

$$X—R^4—X \qquad (4)$$

and further optionally sulfur.

In formulae (2) to (4), $R^1$, $R^2$, $R^3$, $R^4$ and m are as defined above, X is a halogen atom such as Cl, Br or I, and r is a positive number of 1 to 4 on average.

Typical examples of the compound of formula (2) are given below.

(CH₃CH₂O)₃Si—(CH₂)₃—S—(CH₂)₆—Cl
(CH₃CH₂O)₃Si—(CH₂)₃—S₂—(CH₂)₆—Cl
(CH₃CH₂O)₃Si—(CH₂)₃—S—(CH₂)₄—Cl
(CH₃CH₂O)₃Si—(CH₂)₃—S—(CH₂)₁₀—Cl
(CH₃CH₂O)₃Si—(CH₂)₆—S—(CH₂)₆—Cl
(CH₃CH₂O)₃Si—(CH₂)₃—S—(CH₂)₆—Br
(CH₃O)₃Si—(CH₂)₃—S—(CH₂)₆—Cl
(CH₃CH₂O)₂CH₃Si—(CH₂)₃—S—(CH₂)₆—Cl

Typical examples of the compound of formula (3) are given below.
Na₂S
Na₂S₂
Na₂S₃
Na₂S₄

Typical examples of the compound of formula (4) are given below.
Cl—(CH₂)₆—Cl
Cl—(CH₂)₄—Cl
Cl—(CH₂)₁₀—Cl
Br—(CH₂)₆—Br In preparing the compound of formula (2), any desired method may be used. For example, the compound of formula (2) wherein m=1 can be prepared by reacting a compound of the general formula (5):

$$(R^1O)_{(3-p)}(R^2)_pSi—R^3—SH \qquad (5)$$

wherein $R^1$, $R^2$, $R^3$ and p are as defined above, with an alkali alcoholate to form a compound of the general formula (6):

$$(R^1O)_{(3-p)}(R^2)_pSi—R^3—SM \qquad (6)$$

wherein $R^1$, $R^2$, $R^3$ and p are as defined above, and M is an alkali metal, and reacting the compound of formula (6) with a compound of the general formula (4):

$$X—R^4—X \qquad (4).$$

Alternatively, the compound of formula (2) can be prepared by reacting a compound of the general formula (7):

$$(R^1O)_{(3-p)}(R^2)_pSi—R^3—X \qquad (7)$$

wherein $R^1$, $R^2$, $R^3$ and p are as defined above, and X is a halogen atom, with an anhydrous alkali metal sulfide or anhydrous alkali metal polysulfide of the general formula (3):

$$M_2S_r \qquad (3)$$

and optionally a halogen-containing compound of the general formula (4):

$$X—R^4—X \qquad (4)$$

and further optionally sulfur.

Typical examples of the compound of formula (5) are given below.

(CH₃CH₂O)₃Si—(CH₂)₃—SH (CH₃O)₃Si—(CH₂)₃—SH (CH₃CH₂O)₃Si—CH₂CH(CH₃)CH₂—SH (CH₃CH₂O)₃Si—(CH₂)₆—SH (CH₃O)₃Si—(CH₂)₁₀—SH (CH₃CH₂O)₂CH₃Si—(CH₂)₃—SH

Typical examples of the compound of formula (6) are given below.

(CH₃CH₂O)₃Si—(CH₂)₃—SNa (CH₃O)₃Si—(CH₂)₃—SNa (CH₃CH₂O)₃Si—CH₂CH(CH₃)CH₂—SK (CH₃CH₂O)₃Si—(CH₂)₆—SNa (CH₃O)₃Si—(CH₂)₁₀—SK (CH₃CH₂O)₂CH₃Si—(CH₂)₃—SNa

Typical examples of the compound of formula (7) are given below.

(CH₃CH₂O)₃Si—(CH₂)₃—Cl (CH₃O)₃Si—(CH₂)₃—Cl (CH₃CH₂O)₃Si—CH₂CH(CH₃)CH₂—Cl (CH₃CH₂O)₃Si—(CH₂)₆—Br (CH₃O)₃Si—(CH₂)₁₀—Br (CH₃CH₂O)₂CH₃Si—(CH₂)₃—Cl

The anhydrous alkali metal sulfide of formula (3) which can be used herein may be prepared by dehydrating hydrous sodium sulfide, by reacting hydrogen sulfide with an alkali metal alcoholate in an anhydrous state, or by reacting metallic sodium or potassium with sulfur in an anhydrous state. The anhydrous alkali metal polysulfide which can be used herein may be prepared by dehydrating hydrous sodium polysulfide, by reacting the above-mentioned anhydrous alkali metal sulfide with sulfur in an anhydrous state, or by reacting metallic sodium or potassium with sulfur in an anhydrous state.

A solvent is optionally used when the organosilicon compound of the invention is prepared by reacting a halogen-terminated organosilicon compound of formula (2): $(R^1O)_{(3-p)}(R^2)_pSi-R^3-S_m-R^4-X$ with an anhydrous alkali metal sulfide or anhydrous alkali metal polysulfide of formula (3): $M_2S_r$ and optionally a halogen-containing compound of formula (4): $X-R^4-X$ and further optionally sulfur. Examples of the solvent, if used, include hydrocarbons such as pentane, hexane, heptane, octane, benzene, toluene and xylene, alcohols such as methanol and ethanol, ethers such as dibutyl ether, tetrahydrofuran and dioxane, ketones such as methyl ethyl ketone and methyl isobutyl ketone, esters such as ethyl acetate, and amides such as dimethylformamide. Of these, the alcohols such as methanol and ethanol are preferred.

The reaction temperature generally ranges from about 0° C. to about 150° C., and preferably from about 50° C. to about 100° C. The reaction is continued until the alkali metal sulfide or alkali metal polysulfide disappears, and the reaction time is usually about 30 minutes to about 20 hours.

An arbitrary procedure may be taken for the reaction to take place. In one exemplary procedure, the compound of formula (3) and optionally, sulfur and a solvent are fed to a reactor, to which the compound of formula (2), optionally in admixture with the compound of formula (4) is added dropwise. It is also acceptable that dropwise addition of the compound of formula (2) is followed by dropwise addition of the compound of formula (4). Alternatively, the compound of formula (2) and optionally, the compound of formula (4) and further optionally, sulfur and a solvent are fed to a reactor, into which the compound of formula (3) is slowly introduced.

For the reaction, the respective components are preferably used in an appropriate molar ratio. The molar ratio of the halogen-terminated organosilicon compound of formula (2) to the anhydrous alkali metal sulfide or polysulfide of formula (3) is preferably such that the molar ratio of halogen in the compound of formula (2) to alkali metal in the compound of formula (3) is from 1/0.9 to 1/1.1. The amount of sulfur, if added, is at least (n-r) mole.

When the halogen-containing compound of formula (4) is additionally reacted, the molar ratio of the halogen-terminated organosilicon compound of formula (2) to the halogen-containing compound of formula (4) may be from 1/0.5 to 1/1.5. At the same time, the molar ratio of the compound of formula (4) to the anhydrous alkali metal sulfide or polysulfide of formula (3) is preferably such that the molar ratio of [halogen in the compound of formula (2) plus halogen in the compound of formula (4)] to alkali metal in the compound of formula (3) is from 1/0.9 to 1/1.1.

In another embodiment, the organosilicon compound of the invention can be prepared directly by reacting a compound of formula (7):

$$(R^1O)_{(3-p)}(R^2)_pSi-R^3-X \quad (7)$$

wherein $R^1$, $R^2$, $R^3$ and p are as defined above, and X is a halogen atom with an anhydrous alkali metal sulfide or anhydrous alkali metal polysulfide of the general formula (3):

$$M_2S_r \quad (3)$$

and optionally a halogen-containing compound of the general formula (4):

$$X-R^4-X \quad (4)$$

and further optionally sulfur, as long as the molar ratio of the respective components is properly adjusted. It is noted that this direct method is difficult to prepare the compounds of formula (1) wherein m<n which are preferred in the present invention.

In a further embodiment, the organosilicon compound of the invention can be prepared directly by reacting a compound of the average compositional formula (8):

$$X-R^4-(S_n-R^4)_q-X \quad (8)$$

wherein $R^4$, X, n and q are as defined above and a compound of the general formula (7):

$$(R^1O)_{(3-p)}(R^2)_pSi-R^3-X \quad (7)$$

with an anhydrous alkali metal sulfide or anhydrous alkali metal polysulfide of the general formula (3):

$$M_2S_r \quad (3)$$

and optionally sulfur. It is noted that this method is difficult to prepare the compounds of formula (1) wherein m<n which are preferred in the present invention, because equilibration reaction of sulfide chains takes place.

In a still further embodiment, the organosilicon compound of the invention can be prepared by reacting a compound of the average compositional formula (9):

$$(R^1O)_{(3-p)}(R^2)_pSi-R^3-SH \quad (9)$$

wherein $R^1$, $R^2$, $R^3$ and p are as defined above and a compound of the general formula (10):

$$HS-R^4-SH \quad (10)$$

wherein $R^4$ is as defined above with sulfur dichloride or disulfur dichloride of the general formula (3a):

$$S_sCl_2 \quad (3a)$$

wherein s is 1 or 2 in the presence of a hydrochloric acid scavenger. It is noted that this method is difficult to prepare the compounds of formula (1) wherein m<n which are preferred in the present invention, because the average number of sulfide chains is 4.

The organosilicon compound of the average compositional formula (1) according to the invention is effectively used as a compounding agent for rubber. Therefore, the invention provides a rubber compounding agent comprising the organosilicon compound of the average compositional formula (1). The compounding agent of the invention is advantageously used in silica-loaded rubber compositions. The rubber compounding agent may comprise the organosilicon compound alone, or the organosilicon compound in admixture with a powder, or the organosilicon compound in admixture with another compounding agent.

In the embodiment wherein the compounding agent is a mixture of (A) the organosilicon compound and (B) a powder, examples of the powder are carbon black, talc, calcium carbonate, stearic acid and silica, with silica being preferred. The organosilicon compound (A) and the powder (B) are mixed in a weight ratio (A)/(B) between 70/30 and 5/95 and preferably between 60/40 and 30/70. With too small an amount of the powder, reaction of the powder with the organosilicon compound of formula (1) proceeds too fast, leading to a lowering of reinforcement. With too large an amount of the powder, the surface treatment effect of the organosilicon compound of formula (1) on the powder is weakened.

The rubber composition to which the compounding agent of the invention is applicable includes a rubber as a base. The base rubber may be any of ordinary rubbers which are commonly compounded in conventional rubber compositions, for example, natural rubber (NR), diene rubbers such as polyisoprene rubber (IR), styrene-butadiene copolymer rubbers (SBR), polybutadiene rubbers (BR), acrylonitrile-butadiene copolymer rubbers (NBR) and butyl rubber (IIR), as well as ethylene-propylene copolymer rubbers (e.g., EPR and EPDM), alone or in blends thereof.

In these rubber compositions, the organosilicon compound of the invention can also serve as a substitute for the silane coupling agent although it is acceptable to add another silane coupling agent. Any desired one of silane coupling agents which are commonly used with silica fillers may be added. Typical examples include vinyltrimethoxysilane, vinyltriethoxysilane, γ-glycidoxypropyltrimethoxysilane, γ-aminopropyltriethoxysilane, β-aminoethyl-γ-aminopropyl-trimethoxysilane, γ-mercaptopropyltrimethoxysilane, γ-mercaptopropyltriethoxysilane, γ-methacryloxypropyl-trimethoxysilane, bis(triethoxysilylpropyl) tetrasulfide, and bis(triethoxysilylpropyl) disulfide. Of these, bis(triethoxysilylpropyl) tetrasulfide and bis(triethoxysilylpropyl) disulfide are preferred.

The compounding agent comprising the organosilicon compound of the average compositional formula (1) is preferably added to a rubber composition in such amounts that 0.2 to 30 parts by weight, more preferably 1 to 20 parts by weight of the organosilicon compound is present per 100 parts by weight of the base rubber. Too small an amount of the organosilicon compound may fail to achieve the desired effect.

In addition to the essential components described above, the rubber composition to which the compounding agent of the invention is applicable may further include various additives which are commonly incorporated in tires and ordinary rubbers, such as, for example, carbon black, vulcanizing or crosslinking agents, vulcanizing or crosslinking accelerators, various oils, antioxidants, fillers, and plasticizers. These additives may be mixed with the base rubber and other components in a conventional manner to form a rubber composition which is ready for vulcanization or crosslinking. The amounts of these additives may be conventional amounts as long as the objects of the invention are not impaired.

EXAMPLE

Synthesis Examples, Examples and Comparative Examples are given below for illustrating the invention although they should not be construed as limiting the invention thereto. All parts are by weight. The abbreviations have the following meanings.

| | |
|---|---|
| IR: | infrared absorption spectroscopy |
| $^1$H-NMR: | proton nuclear magnetic resonance spectroscopy |
| MS: | mass spectrometry |
| SFC: | supercritical fluid chromatography |
| GPC: | gel permeation chromatography |

Synthesis Example 1

A 1-liter separable flask equipped with a nitrogen gas inlet, thermometer, Dimroth condenser and dropping funnel was charged with 119 g (0.5 mol) of 3-mercaptopropyltriethoxy-silane. With stirring, 151.2 g (0.45 mol) of a 20% ethanol solution of sodium ethylate was added dropwise. After the completion of dropwise addition, the solution was heated at 80° C. and continuously stirred for 3 hours. Thereafter, the solution was cooled and transferred to a dropping funnel.

A 1-liter separable flask equipped with a nitrogen gas inlet, thermometer, Dimroth condenser and dropping funnel was charged with 310.0 g (2.0 mol) of 1,6-dichlorohexane and heated at 80° C. With stirring, the reaction product of 3-mercaptopropyltriethoxysilane with sodium ethylate was slowly added dropwise. After the completion of dropwise addition, the solution was continuously stirred at 80° C. for 5 hours, and then cooled. From the solution, the salt was filtered off and the ethanol and excess 1,6-dichlorohexane were distilled off in vacuum. The residual solution was subjected to vacuum distillation, collecting 64.2 g of a colorless clear liquid at a boiling point of 148–150° C./0.005 Torr. On analysis by IR, $^1$H-NMR and MS, the liquid was identified to be a compound of the following formula.

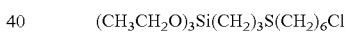

$(CH_3CH_2O)_3Si(CH_2)_3S(CH_2)_6Cl$

Analysis by gas chromatography gave a purity of 98.7%.

Example 1

A 500-ml separable flask equipped with a nitrogen gas inlet, thermometer, Dimroth condenser and dropping funnel was charged with 80 g of ethanol, 5.46 g (0.07 mol) of anhydrous sodium sulfide, and 2.24 g (0.07 mol) of sulfur and heated at 80° C. With stirring, 49.91 g (0.14 mol) of the compound of the formula:

$(CH_3CH_2O)_3Si(CH_2)_3S(CH_2)_6Cl$, synthesized in Synthesis Example 1, was slowly added dropwise. After the completion of dropwise addition, the solution was continuously stirred at 80° C. for 10 hours, and then cooled. From the solution, the salt formed was filtered off and the ethanol solvent was distilled off in vacuum, yielding 46.3 g of a reddish brown clear liquid. On analysis by IR, $^1$H-NMR, SFC and MS, the liquid was identified to be a compound of the following average compositional formula.

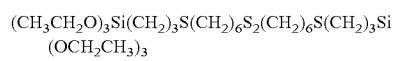

$(CH_3CH_2O)_3Si(CH_2)_3S(CH_2)_6S_2(CH_2)_6S(CH_2)_3Si(OCH_2CH_3)_3$

Analysis by GPC showed that the monomer had a purity of 89.7%.

The results of MS are shown below.

|  | C | H | S | Si |
|---|---|---|---|---|
| Calculated, % | 50.9 | 9.4 | 18.1 | 7.9 |
| Found, % | 50.5 | 9.2 | 18.3 | 8.0 |

Example 2

Synthesis was carried out as in Example 1 except that the amount of sulfur was changed from 2.24 g to 4.48 g (0.14 mol). There was obtained 48.1 g of a reddish brown clear liquid. On analysis by IR, $^1$H-NMR, SFC and MS, the liquid was identified to be a compound of the following average compositional formula.

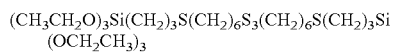

$(CH_3CH_2O)_3Si(CH_2)_3S(CH_2)_6S_3(CH_2)_6S(CH_2)_3Si(OCH_2CH_3)_3$

Analysis by GPC showed that the monomer had a purity of 88.3%.

The results of MS are shown below.

|  | C | H | S | Si |
|---|---|---|---|---|
| Calculated, % | 48.7 | 9.0 | 21.7 | 7.6 |
| Found, % | 48.4 | 8.8 | 22.0 | 7.8 |

Example 3

Synthesis was carried out as in Example 1 except that the amount of sulfur was changed from 2.24 g to 6.72 g (0.21 mol). There was obtained 50.3 g of a reddish brown clear liquid. On analysis by IR, $^1$H-NMR, SFC and MS, the liquid was identified to be a compound of the following average compositional formula.

$(CH_3CH_2O)_3Si(CH_2)_3S(CH_2)_6S_4(CH_2)_6S(CH_2)_3Si(OCH_2CH_3)_3$

Analysis by GPC showed that the monomer had a purity of 88.9%.

The results of MS are shown below.

|  | C | H | S | Si |
|---|---|---|---|---|
| Calculated, % | 46.7 | 8.6 | 24.9 | 7.3 |
| Found, % | 46.4 | 8.4 | 25.2 | 7.6 |

Example 4

Synthesis was carried out as in Example 1 except that 57.75 g (0.14 mol) of the compound of formula: $(CH_3CH_2O)_3Si(CH_2)_3S(CH_2)_{10}Cl$ was used instead of 49.91 g (0.14 mol) of the compound of formula: $(CH_3CH_2O)_3Si(CH_2)_3S(CH_2)_6Cl$. There was obtained 53.8 g of a reddish brown clear liquid. On analysis by IR, $^1$H-NMR, SFC and MS, the liquid was identified to be a compound of the following average compositional formula.

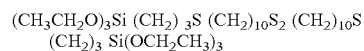

$(CH_3CH_2O)_3Si(CH_2)_3S(CH_2)_{10}S_2(CH_2)_{10}S(CH_2)_3Si(OCH_2CH_3)_3$

Analysis by GPC showed that the monomer had a purity of 85.9%.

The results of MS are shown below.

|  | C | H | S | Si |
|---|---|---|---|---|
| Calculated, % | 55.7 | 10.1 | 15.7 | 6.9 |
| Found, % | 55.3 | 9.7 | 16.0 | 7.3 |

Example 5

Synthesis was carried out as in Example 2 except that 54.39 g (0.14 mol) of the compound of formula: $(CH_3CH_2O)_3Si(CH_2)_3S_2(CH_2)_6Cl$ was used instead of 49.91 g (0.14 mol) of the compound of formula: $(CH_3CH_2O)_3Si(CH_2)_3S(CH_2)_6Cl$. There was obtained 50.8 g of a reddish brown clear liquid. On analysis by IR, $^1$H-NMR and MS, the liquid was identified to be a compound of the following average compositional formula.

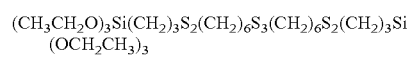

$(CH_3CH_2O)_3Si(CH_2)_3S_2(CH_2)_6S_3(CH_2)_6S_2(CH_2)_3Si(OCH_2CH_3)_3$

On analysis by GPC, a distribution of sulfur due to equilibration reaction was confirmed, finding that the compound was not of high purity, but merely an average composition.

The results of MS are shown below.

|  | C | H | S | Si |
|---|---|---|---|---|
| Calculated, % | 44.9 | 8.3 | 27.9 | 7.0 |
| Found, % | 44.3 | 8.0 | 28.3 | 7.2 |

Example 6

Synthesis was carried out as in Example 1 except that the amount of anhydrous sodium sulfide was changed from 5.46 g (0.07 mol) to 10.92 g (0.14 mol), the amount of sulfur was changed from 2.24 g (0.07 mol) to 4.48 g (0.14 mol), and a mixture of 49.91 g (0.14 mol) of the compound of formula: $(CH_3CH_2O)_3Si(CH_2)_3S(CH_2)_6Cl$ and 10.85 g (0.07 mol) of 1,6-dichlorohexane was used instead of 49.91 g (0.14 mol) of the compound of formula: $(CH_3CH_2O)_3Si(CH_2)_3S(CH_2)_6Cl$. There was obtained 55.1 g of a reddish brown clear liquid. On analysis by IR, $^1$H-NMR and MS, the liquid was identified to be a compound of the following average compositional formula.

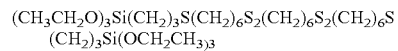

$(CH_3CH_2O)_3Si(CH_2)_3S(CH_2)_6S_2(CH_2)_6S_2(CH_2)_6S(CH_2)_3Si(OCH_2CH_3)_3$

On analysis by GPC, a wide distribution of sulfur was confirmed, finding that the compound was not of high purity, but merely an average composition.

The results of MS are shown below.

|  | C | H | S | Si |
|---|---|---|---|---|
| Calculated, % | 50.5 | 9.2 | 22.5 | 6.6 |
| Found, % | 50.1 | 9.0 | 22.9 | 6.8 |

Examples relating to the rubber compounding agent are given below. Samples were prepared as follows.

Preparation of Samples

A master batch was prepared by compounding together 110 parts of an oil-extended emulsion polymerization SBR (#1712 by JSR Corp.), 20 parts of NR (ordinary RSS #3 grade), 20 parts of carbon black (ordinary N234 grade), 50 parts of silica (Nipsil AQ by Nippon Silica Industry Co., Ltd.), 6.5 parts of the compound of Examples 1 to 6 or the comparative compound, shown below, 1 part of stearic acid, and 1 part of an antioxidant (Nocrac 6C by Ouchi Shinko Chemical Co., Ltd.). To the master batch were added 3.0 parts of zinc white, 0.5 part of a vulcanizing accelerator DM (dibenzothiazyl disulfide), 1.0 part of a vulcanizing accelerator NS (N-t-butyl-2-benzothiazolylsulphenamide) and 1.5 parts of sulfur. They were kneaded to form a rubber composition. In a mold of 15×15×0.2 cm, the rubber composition was press vulcanized at 160° C. for 15 minutes into a test specimen (rubber sheet), which was examined for vulcanized physical properties.

The test methods for determining physical properties of compositions are described below.

Unvulcanized Physical Properties

1) Mooney viscosity: According to JIS K6300, measurement was made under conditions: preheating 1 minute, measurement 4 minutes, and temperature 130° C. The measurement result was expressed as an index based on 100 for Comparative Example 1. A lower index corresponds to a lower Mooney viscosity and indicates better processability.

Vulcanized Physical Properties 1) 300% deformation stress, tensile strength: Measurement was made according to JIS K6251. The measurement result was expressed as an index based on 100 for Comparative Example 1. A higher index corresponds to greater 300% deformation stress and tensile strength.

2) Resilience: Measurement was made according to JIS K6252. The measurement result was expressed as an index based on 100 for Comparative Example 1. A higher index corresponds to a greater resilience.

3) tan δ: Using a viscoelasticity meter (Rheometric Scientific Inc.), measurement was made under conditions: tensile dynamic strain 5%, frequency 15 Hz and 60° C. The test specimen was a sheet of 0.2 cm thick and 0.5 cm wide, the clamp span was 2 cm, and the initial weight was 160 g. The value of tan δ was expressed as an index based on 100 for Comparative Example 1. A lower index corresponds to a smaller hysteresis loss and lower heat generation.

Examples 7–13 and Comparative Examples 1–3

These Examples are to evaluate the rubber compounding agents according to the invention. The results of evaluation are shown in Table 1.

The comparative compounds used in Comparative Examples 1 to 3 are shown below.

Comparative Compound 1

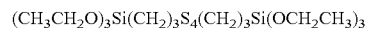
$(CH_3CH_2O)_3Si(CH_2)_3S_4(CH_2)_3Si(OCH_2CH_3)_3$

Comparative Compound 2

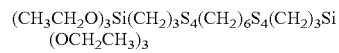
$(CH_3CH_2O)_3Si(CH_2)_3S_4(CH_2)_6S_4(CH_2)_3Si(OCH_2CH_3)_3$

Comparative Compound 3

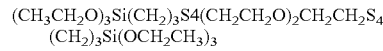
$(CH_3CH_2O)_3Si(CH_2)_3S_4(CH_2CH_2O)_2CH_2CH_2S_4(CH_2)_3Si(OCH_2CH_3)_3$ In Example 13, the amount of carbon black compounded was changed to 13.5 parts, and 13 parts of a compounding agent consisting of 6.5 parts of the compound of Example 1 and 6.5 parts of carbon black N234 was added.

TABLE 1

| Ingredients (pbw) | Example | | | | | | | Comparative Example | | |
|---|---|---|---|---|---|---|---|---|---|---|
| | 7 | 8 | 9 | 10 | 11 | 12 | 13 | 1 | 2 | 3 |
| SBR | 110.0 | 110.0 | 110.0 | 110.0 | 110.0 | 110.0 | 110.0 | 110.0 | 110.0 | 110.0 |
| NR | 20.0 | 20.0 | 20.0 | 20.0 | 20.0 | 20.0 | 20.0 | 20.0 | 20.0 | 20.0 |
| Carbon black | 20.0 | 20.0 | 20.0 | 20.0 | 20.0 | 20.0 | 13.5 | 20.0 | 20.0 | 20.0 |
| Silica | 50.0 | 50.0 | 50.0 | 50.0 | 50.0 | 50.0 | 50.0 | 50.0 | 50.0 | 50.0 |
| Stearic acid | 1.0 | 1.0 | 1.0 | 1.0 | 1.0 | 1.0 | 1.0 | 1.0 | 1.0 | 1.0 |
| Nocrac 6C | 1.0 | 1.0 | 1.0 | 1.0 | 1.0 | 1.0 | 1.0 | 1.0 | 1.0 | 1.0 |
| Zinc white | 3.0 | 3.0 | 3.0 | 3.0 | 3.0 | 3.0 | 3.0 | 3.0 | 3.0 | 3.0 |
| DM | 0.5 | 0.5 | 0.5 | 0.5 | 0.5 | 0.5 | 0.5 | 0.5 | 0.5 | 0.5 |
| NS | 1.0 | 1.0 | 1.0 | 1.0 | 1.0 | 1.0 | 1.0 | 1.0 | 1.0 | 1.0 |
| Sulfur | 1.5 | 1.5 | 1.5 | 1.5 | 1.5 | 1.5 | 1.5 | 1.5 | 1.5 | 1.5 |
| Compound of Example 1 | 6.5 | — | — | — | — | — | — | — | — | — |
| Compound of Example 2 | — | 6.5 | — | — | — | — | — | — | — | — |
| Compound of Example 3 | — | — | 6.5 | — | — | — | — | — | — | — |
| Compound of Example 4 | — | — | — | 6.5 | — | — | — | — | — | — |
| Compound of Example 5 | — | — | — | — | 6.5 | — | — | — | — | — |
| Compound of Example 6 | — | — | — | — | — | 6.5 | — | — | — | — |
| Mixture of compound of Example 1 and carbon black | — | — | — | — | — | — | 13.0 | — | — | — |
| Comparative Compound 1 | — | — | — | — | — | — | — | 6.5 | — | — |
| Comparative Compound 2 | — | — | — | — | — | — | — | — | 6.5 | — |
| Comparative Compound 3 | — | — | — | — | — | — | — | — | — | 6.5 |

TABLE 1-continued

| Ingredients | Example | | | | | | | Comparative Example | | |
|---|---|---|---|---|---|---|---|---|---|---|
| (pbw) | 7 | 8 | 9 | 10 | 11 | 12 | 13 | 1 | 2 | 3 |
| Unvulcanized physical properties | | | | | | | | | | |
| Mooney viscosity | 93 | 95 | 94 | 92 | 98 | 97 | 96 | 100 | 103 | 99 |
| Vulcanized physical properties | | | | | | | | | | |
| 300% deformation stress | 120 | 122 | 125 | 126 | 117 | 112 | 116 | 100 | 106 | 97 |
| Tensile strength | 105 | 106 | 106 | 107 | 103 | 102 | 108 | 100 | 100 | 98 |
| Resilience | 112 | 110 | 110 | 111 | 108 | 106 | 109 | 100 | 103 | 96 |
| tanδ (60° C.) | 79 | 81 | 80 | 79 | 85 | 88 | 85 | 100 | 96 | 102 |

There have been described organosilicon compounds which are effective as a compounding agent for organic/inorganic composite materials and as a filler treating agent, and especially useful as a compounding agent for rubber. The method of the invention ensures preparation of the organosilicon compounds. Using compounding agents comprising the organosilicon compounds, rubber compositions are improved in various physical properties including tensile strength, resilience and tan δ.

The invention claimed is:

1. An organosilicon compound of the average compositional formula (1):

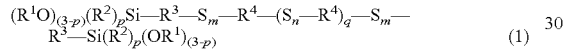
 (1)

wherein $R^1$ and $R^2$ each are a monovalent hydrocarbon group having 1 to 4 carbon atoms, $R^3$ and $R^4$ each are a divalent hydrocarbon group having 1 to 15 carbon atoms, m is a positive number of 1 to 3 on average, n is a positive number of 2 to 4 on average, m<n, p is 0, 1 or 2, and q is 1, 2 or 3.

2. The organosilicon compound of claim 1 wherein in formula (1), m is 1 and n is a positive number of 2 to 3 on average.

3. A rubber compounding agent comprising the organosilicon compound of claim 1.

4. A rubber compounding agent comprising the organosilicon compound of claim 1 and at least one powder in a weight ratio between 70/30 and 5/95.

5. An organosilicon compound of claim 1 of the formula:

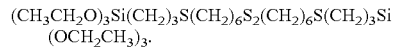

6. An organosilicon compound of claim 1 of the formula:

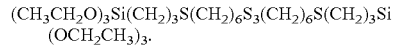

7. An organosilicon compound of claim 1 of the formula:

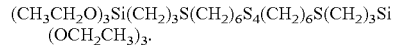

8. An organosilicon compound of claim 1 of the formula:

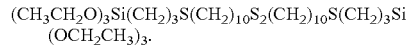

9. An organosilicon compound of claim 1 of the formula:

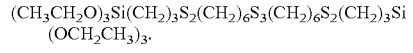

10. An organosilicon compound of claim 1 of the formula:

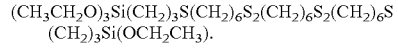

* * * * *